United States Patent [19]
Jung et al.

[11] Patent Number: 5,674,194
[45] Date of Patent: Oct. 7, 1997

[54] PROCESS CONTROL SYSTEM

[75] Inventors: Christopher C. Jung, Mission Viejo, Calif.; Douglas E. Wallace, Jr., Austin, Tex.

[73] Assignee: Alcon Laboratories Inc., Fort Worth, Tex.

[21] Appl. No.: 548,126

[22] Filed: Oct. 25, 1995

[51] Int. Cl.$^6$ .................................................. A61M 1/00
[52] U.S. Cl. ............................................. 604/65; 604/118
[58] Field of Search ................................. 604/23, 26–28, 604/30–31, 65–67, 93, 118–119, 121, 131–133, 140, 141, 147, 149, 246

[56] References Cited

U.S. PATENT DOCUMENTS

| | | |
|---|---|---|
| 4,274,411 | 6/1981 | Dotson, Jr. . |
| 4,395,258 | 7/1983 | Wang et al. . |
| 4,622,503 | 11/1986 | Sundblom et al. . |
| 4,705,067 | 11/1987 | Coffe .................................. 137/487.5 |
| 4,706,687 | 11/1987 | Rogers . |
| 4,757,814 | 7/1988 | Wang et al. . |
| 4,770,654 | 9/1988 | Rogers et al. . |
| 5,094,260 | 3/1992 | Stuart et al. . |
| 5,354,268 | 10/1994 | Peterson et al. .................. 604/35 |
| 5,380,280 | 1/1995 | Peterson . |
| 5,520,652 | 5/1996 | Peterson ........................... 604/119 |

*Primary Examiner*—Manuel Mendez
*Attorney, Agent, or Firm*—Jeffrey S. Schira

[57] ABSTRACT

A process control system according to the present invention uses analog control circuitry in which a differential amplifier stage is incorporated into the feedback path rather that the feedforward path to enable the control of highly non-linear processes that may also exhibit high levels of hysteresis. Such processes often have superior performance characteristics that conventional control circuitry cannot exploit. The present invention additionally incorporates an automatic control circuit which varies the gain of various stages the control circuitry when the output of the process is within a predetermined range. An embodiment of the present invention is used to control a nonlinear proportional valve with severe hysteresis. The valve regulates the pressure within pressure-driven ophthalmic surgical instruments, which must be controlled extremely precisely to enable successful eye surgery.

14 Claims, 5 Drawing Sheets

PROCESS CONTROL SYSTEM

This invention relates generally to an apparatus for controlling a mechanical, pneumatic, and/or electrical process. More particularly, the invention relates to an apparatus for controlling the pressure within an ophthalmic surgical device. Such devices include pneumatic scissors and other devices driven by positive gage pressure and suction probes that employ negative gage pressure.

BACKGROUND OF THE INVENTION

During ophthalmic surgery, surgeons insert extremely small pneumatic surgical instruments (typically of approximately 0.036" outside diameter) into the patient's eye to manipulate tissue. These instruments often include suction (aspiration) lines to evacuate excised tissue. To avoid mistakenly damaging healthy tissue, the control of the aspiration and operating pressures in the instrument must be very precise.

Conventional systems often employ proportional valves to control pressure. Vacuum is generated by feeding the output of the proportional valve to a venturi. For suction probes the venturi typically is connected to a fixed-volume debris receptacle that communicates pneumatically with the probe. Vacuum within the debris receptacle is regulated by controlling the flow of air through the proportional valve and thus through the venturi. Systems that control positive drive pressure used to control pneumatic scissors and other positive-gage-pressure devices employ the proportional valve, but not the venturi.

Conventional pneumatic control systems typically employ a proportional valve exhibiting a flow rate that is approximately linearly proportional to the voltage of the control signal. Such approximately linear response is required to enable conventional analog circuitry to control acceptably the proportional valve and thus the pressure at the surgical instrument.

Typically, the surgeon controls the pressure in an instrument with an input device, often a foot-actuated pedal, that generates a desired control signal. If the instrument were not exposed to environments that resulted in varying pressure loads and if the responses of the pneumatic components were more uniform, the desired pressure signal could be used directly (e.g., through a conventional voltage follower with current boost amplifier) to position the proportional valve and control the pressure in the instrument. To compensate dynamically for these variations in the environment and the components of the instrument, conventional control circuitry incorporates feedback in the control loop.

The dynamic pressure in the instrument is continuously measured by a pressure transducer connected to the pneumatic manifold feeding the instrument, which generates an actual pressure signal that varies approximately linearly with the measured pressure. This actual pressure signal is compared to the desired pressure signal and the difference (the "error signal") is used to generate an appropriate control signal for the proportional valve. The proportional valve adjusts according to the control signal, which changes the air flow rate through the valve and thus the air pressure in the instrument.

Conventional analog control circuits employ various combinations of proportional, integral, and differential amplifier stages in the feedforward path (the path between the voltage comparator and the pressure transducer). Each of the amplifiers may employ its own operational amplifier or be combined with other stages into a circuit employing a single operational amplifier. To achieve a given set of pneumatic performance requirements, the more linear the response of the proportional valve, the fewer stages required in the control circuit to maintain stability.

The simplest control circuit employs only proportional mode control in the feedforward path. Other, more sophisticated, conventional control circuits employ proportional and integral mode control in the feedforward path. An even more sophisticated conventional control circuit employs proportional, integral, and differential mode control in the feedforward path, a so-called PID control circuit. Proportional mode control adequately performs the basic control functions because it can respond to relatively gradual changes in the error signal. Integral mode control allows the circuit to compensate for any residual steady-state error. Differential mode control allows the circuit to respond quickly to transient error signals.

Some conventional pressure control systems, which generate vacuum and employ linear proportional valves and control circuitry in the feedforward path, exhibit acceptable rise/fall times of approximately 300 milliseconds. However, they are unable to maintain high vacuum levels when the instrument is exposed to air leakage because the linear valve/venturi combination does not have the capacity to overcome the leakage. Particularly, the vacuum generation system disclosed by U.S. Pat. No. 4,770,654 to Rogers, et al. generates only 250 mm Hg of vacuum at sea level when its instrument is exposed to a leakage rate of approximately 30 cc/sec.

Another conventional system, which is made by Storz Instrument Company and uses a linear proportional valve and control circuitry in the feedforward path, exhibits superior immunity to leakage but at the expense of a relatively high air consumption rate of approximately 175 standard liters per mute. (SLPM). Air consumption is an important pneumatic performance parameter when the instrument uses an internal air source because the rate of air consumption determines how long an instrument may be used without changing the air tank in the pressure control system. Typically, such tanks contain one cubic foot of air under 200 atmospheres pressure when full. The amount of time that a given system can generate vacuum is inversely proportional to the air consumption rate. Eye surgery often requires up to one hour of vacuum generation.

Nonlinear proportional valves exist that exhibit pneumatic performance superior to that of the approximately linear proportional valves used in conventional pressure control systems. For example, the pressure control system of the present invention uses a mass flow control valve (a nonlinear proportional valve), a vacuum pump, and a 60 cc vacuum chamber to maintain a 300 millisecond response time, generate up to approximately 600 mm Hg vacuum, and maintain 250 mm Hg vacuum at leakage rates up to 185 cc/sec. The preferred valve used with the present invention consumes only 40 SLPM, which allows about 3–4 surgical procedures to be performed using one tank. However, valves of the type preferred with the present invention can exhibit nonlinearity and hysteresis for which conventional PID control circuitry will not compensate acceptably.

SUMMARY OF THE INVENTION

The present invention employs analog control circuitry that enables the use of nonlinear proportional valves, with their sometimes superior pneumatic performance, in ophthalmic pressure-controlled instruments. The control circuitry of the present invention employs proportional and integral amplifier stages in the feedforward path, but incorporates the differential amplifier stage into the feedback path (the path between the pressure transducer and the voltage comparator). The control circuitry of the present invention also includes automatic gain control circuitry that increases the gain of the proportional amplifier stage and decreases the gain of the differential amplifier stage in certain regions of pressure generation, depending on the characteristic response of the valve to drive voltage. This control circuitry, unlike conventional PID control circuitry, is able to compensate for the undesirable nonlinear response and hysteresis of nonlinear proportional valves while fully utilizing the superior pneumatic performance of these nonlinear proportional valves.

It is therefore an object of the present invention to provide a pressure control system for use in ophthalmic surgical devices with increased immunity to air leakage.

It is a further object of the present invention to provide a pressure control system for use in ophthalmic surgical devices with reduced air consumption.

It is still a further object of the present invention to provide a pressure control system for use in ophthalmic surgical devices that is capable of generating up to 600 mm Hg vacuum at sea level.

Other objects, features, and advantages of the present invention will become apparent with reference to the remainder of this document.

DETAILED DESCRIPTION OF THE DRAWINGS

Figure 1:
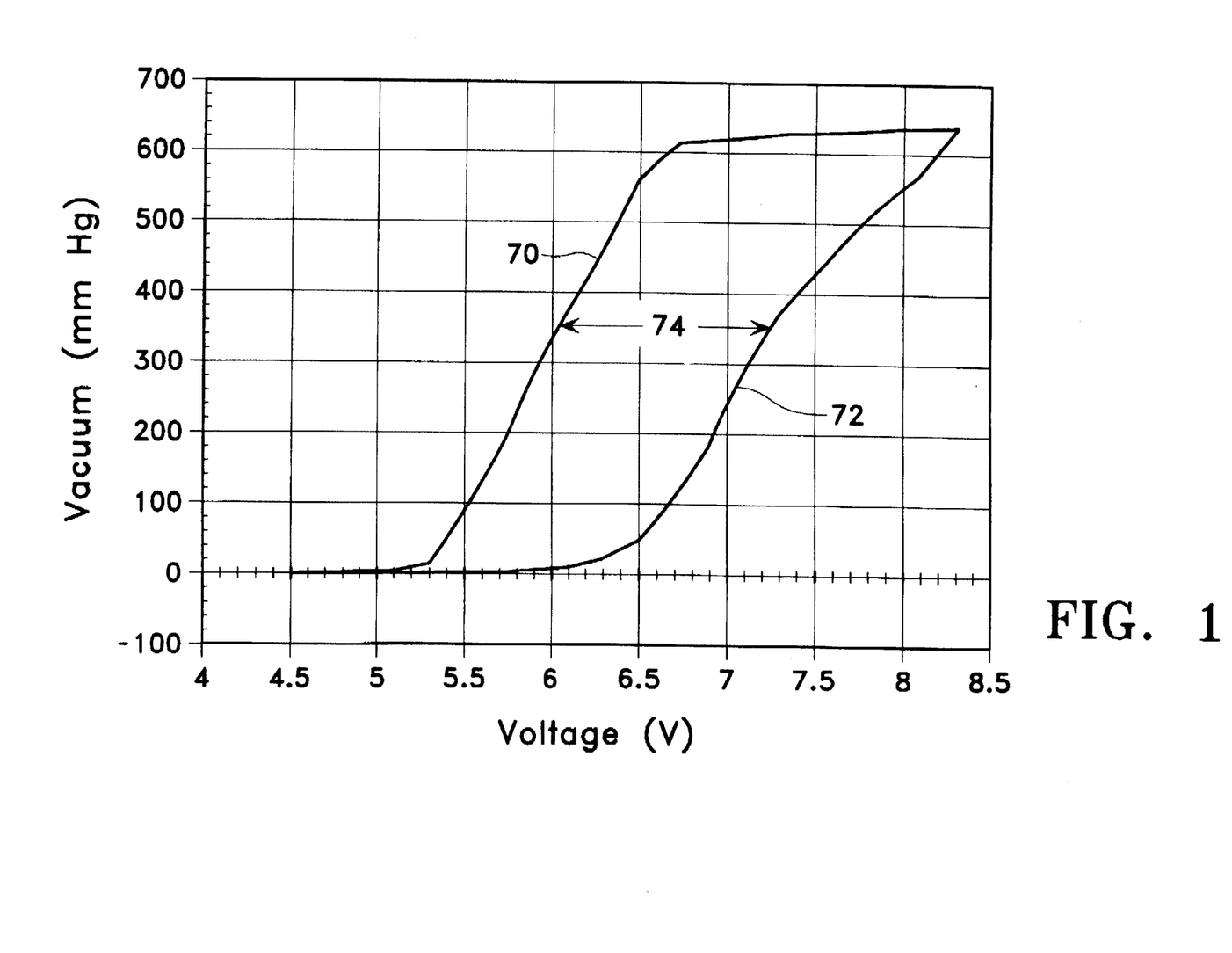
FIG. 1 is a representative plot of generated vacuum versus drive voltage for the combination of the proportional valve and venturi used in one embodiment of the present invention.

FIG. 1 is a representative plot of generated vacuum versus drive voltage for the combination of a preferred nonlinear proportional valve and vacuum pump, the combination used in one embodiment of the present invention, when supplied by a regulated pressure source of about 50–60 psi. One suitable nonlinear proportional valve is Model No. 002-AXXAVCAA, available from Porter Instrument Company, Inc., Hatfield, Pa., although other suitable nonlinear proportional valves may also be used. One suitable vacuum pump (venturi) is Model No. LX10, available from PIAB, Hingham, Mass., but other suitable vacuum pumps may also be used. At drive voltages of less than approximately 5 volts, the valve opens especially slowly as drive voltage is increased, as is apparent from the very shallow slope of opening trace 72 in the range of about 5.5–6.5 volts drive voltage (corresponding to about 0–50 mm Hg vacuum). Opening trace 72 indicates that, as the drive voltage increases, the valve opens more quickly (note the steeper slope of opening trace 72 in the range of about 6.5–7.5 volts). As indicated by closing trace 70, decreasing the drive voltage after the valve is fully opened results in the valve closing such that the valve eventually is again fully closed and no vacuum is generated. Closing trace 70 is also nonlinear and moreover does not correspond to opening trace 72. Thus, the hysteresis of the valve/venturi combination is evident by the gap 74 between opening trace 72 and closing trace 70. The nonlinearity and hysteresis of this valve/venturi combination cannot be adequately compensated for by conventional PID control circuitry such that this valve/venturi can be used to drive ophthalmic surgical instruments.

Figure 2:
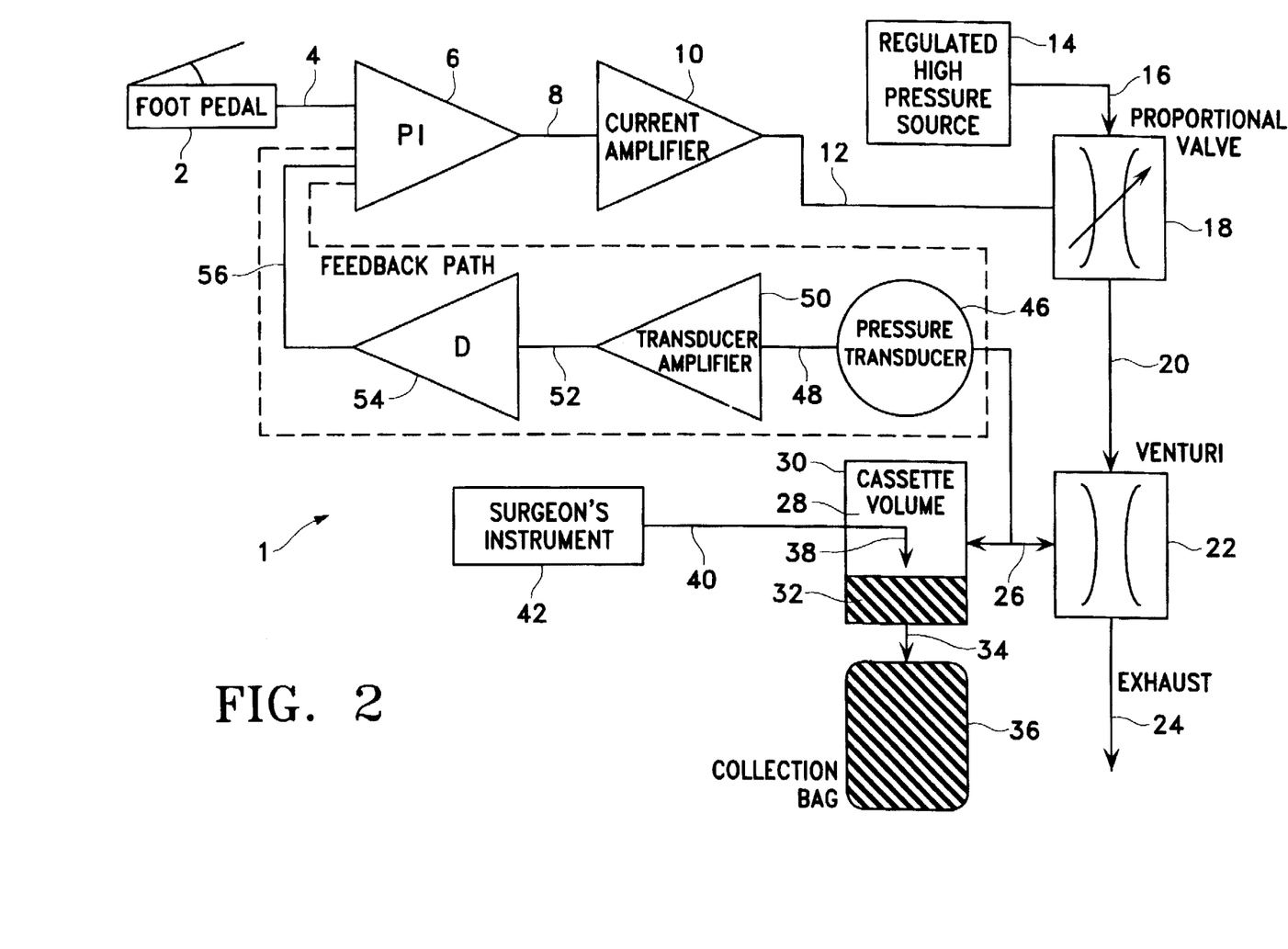
FIG. 2 is a block diagram of one embodiment of the pressure control system of the present invention.

FIG. 2 is a block diagram of an embodiment of the pressure control system 1 that is configured to generate vacuum for a suction probe. The surgeon chooses the desired vacuum level by manipulating an input device 2, for example, a foot pedal, to generate input signal 4. When the system 1 is operating, proportional/integral amplifier stage 6 applies gain to the difference between input signal 4 and feedback signal 56, which results in proportional/integral output signal 8. Proportional/integral output signal 8 is fed to voltage follower with current boost stage 10 so that drive signal 12 is of sufficient current to open and close proportional valve 18.

Regulated high pressure source 14 of approximately 50–60 psi is connected via input manifold 16 to proportional valve 18. The degree to which proportional valve 18 is open determines the pressure and air flow rate in valve output manifold 20, which connects proportional valve 18 to venturi 22. Valve output manifold 20 may alternatively be connected to a surgical device that is driven by positive gage pressure such as a pneumatic scissors (not shown) instead of being connected to venturi 22. The air flows through venturi 22 and into exhaust manifold 24 and reduces the pressure in vacuum manifold 26. Vacuum manifold 26 is connected to cassette volume 28 within cassette 30 thus reducing the pressure in cassette volume 28. Instrument manifold 40 is also connected to cassette volume 28. Became instrument manifold 40 is connected to surgical instrument 42, such as a suction probe, the surgeon is able to use the suction at the end of the instrument to manipulate material within the patient's eye. Debris 32 is material that the surgeon has removed from the patient's eye through instrument 42 and instrument manifold 40 and into cassette 30. A constant volume of debris 32 is maintained within cassette 30 by a peristaltic pump (not shown), which pumps excess debris through collection manifold 34 into collection bag 36 for final disposal. The greater the air flow through valve output manifold 20, the lower the pressure in vacuum manifold 26, cassette volume 28, instrument manifold 40, and surgical instrument 42.

Also connected to vacuum manifold 26 is pressure transducer 46, which generates a transducer signal 48 that varies approximately linearly with the pressure in vacuum manifold 26 (and thus cassette volume 28, instrument manifold 40, and instrument 42). Transducer signal 48 is first fed to transducer amplifier 50, which acts as a buffer and applies gain so that the resulting signal, vacuum signal 52, linearly varies approximately 1 volt for each 100 mm Hg of measured pressure. Vacuum signal 52 is fed to the noninverting input of differential amplifier stage 54.

As explained above, differential mode control provides high gain to sharp changes in its input and no gain for steady state input. At very low rates of change in vacuum signal 52 (low frequencies near about 0 Hz) differential amplifier stage 54 provides 0 dB gain (unity gain). As the rate of change (frequency) of vacuum signal 52 increases to approximately 14 Hz, differential amplifier stage 54 provides approximately 23 dB gain. The gain provided by differential amplifier stage 54 becomes generally constant at approximately 26 dB for frequencies significantly greater than about 14 Hz. The resulting feedback signal 56 of differential amplifier stage 54 is compared to input signal 4 by proportional/integral amplifier stage 6 at the start of the feedforward path.

To achieve acceptable rise times for the generation of vacuum when valve 18 is operating in shallow slope regions of opening trace 72 and closing trace 70 of FIG. 1, very high gain is required of proportional/integral amplifier stage 6. Therefore, the gain of proportional/integral amplifier stage 6 is set about 10-20 dB higher than a conventional proportional/integral amplifier stage. To prevent proportional/integral amplifier stage 6 from applying too much gain when valve 18 is not operating in a shallow slope region of traces 70 and 72 of FIG. 1, the present invention employs differential amplifier stage 54 in the feedback path (shaded area in FIG. 2), rather than in the feedforward path as in conventional systems. Became it is in the feedback path, differential amplifier stage 54 only generates high voltage differential output signal 56 in response to actual changes in the process being controlled (i.e., after valve 18 actually responds and vacuum is generated). Differential amplifier stage 54, became its output, feedback signal 56, is connected to the inverting input of proportional/integral amplifier stage 6, operates to temper the gain of proportional/integral amplifier stage 6 when sharp changes in vacuum signal 52 occur.

When the surgeon makes a sharp change in the input signal 4 (perhaps a step change in the desired pressure level), proportional/integral amplifier stage 6 applies its high gain and attempts to open valve 18 very quickly with a highly boosted drive signal 12. If this sharp change occurs in a region of opening trace 72 of FIG. 1 with a shallow slope, valve 18 does not respond quickly and vacuum does not change as sharply as input signal 4. Differential amplifier stage 54, because it does not receive a sharp change in vacuum signal 52, does not apply gain and does not temper the high gain of proportional/integral amplifier stage 6. Only when valve 18 actually generates vacuum in response to the highly boosted drive signal 12 will differential amplifier stage 54 temper the gain of proportional/integral amplifier stage 6 to reduce drive signal 12. The overall effect is that the circuit provides unusually high continuous gain when valve 18 is operating in the shallow slope regions of opening trace 72 and closing trace 70 of FIG. 1 until vacuum signal 52 actually changes. Once vacuum signal 52 begins to change, differential amplifier stage 54 provides feedback signal 56 that reduces the gain of proportional/integral amplifier stage 6 to a more conventional level.

The more quickly vacuum signal 52 changes the more quickly differential amplifier stage 54 reduces the gain of proportional/integral amplifier stage 6, which prevents the vacuum in instrument 42 from overshooting the value chosen by the surgeon with input device 2. As long as valve 18 is responding quickly to changes in drive signal 12, differential amplifier stage 54 provides high gain and the gain provided by the proportional/integral amplifier stage 6 remains at conventional levels (i.e., the circuit behaves as a conventional proportional/integral mode control circuit). However, when valve 18 is responding slowly to changes in drive signal 12, differential amplifier stage 54 stops providing as much gain and the gain of the proportional/integral amplifier stage 6 is the substantially boosted gain over that which would maintain a stable conventional control circuit.

Of course, when valve 18 eventually does respond, vacuum signal 52 increases and differential amplifier stage 54 adds gain, which again reduces the gain provided by proportional/integral amplifier stage 6.

By contrast, the differential stage of a conventional PID control circuit responds to sharp changes in the input signal as well as to the vacuum actually generated became the differential stage is in the feedforward path. Thus, when the surgeon makes a sharp change to the input signal of a conventional PID control circuit, the PID stage initially, but temporarily, generates a highly boosted drive signal. However, if the valve does not respond instantly, the overall gain provided by the PID circuit may fall off too quickly because the transient error is no longer present to cause the differential stage of the PID to contribute its gain to drive the valve. Instead, the PID circuit drives the valve based on what now appears to be a steady state error and only the proportional/integral amplifier stages will contribute gain to drive the valve.

Figure 3:
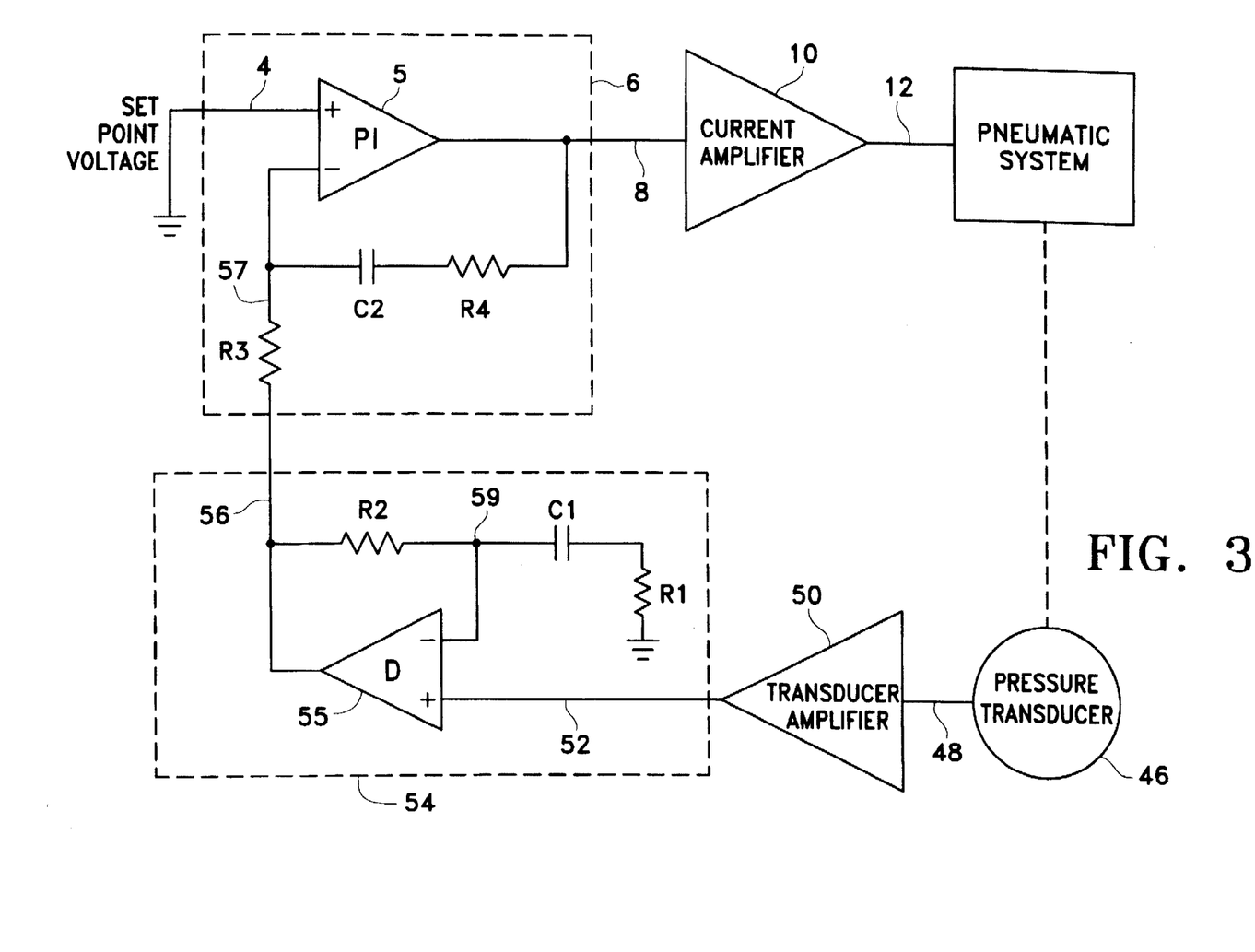
FIG. 3 is a schematic representation of the analog control circuitry of the embodiment of the present invention illustrated in FIG. 2.

FIG. 3 schematically illustrates simplified versions of the differential amplifier stage 54 and proportional/integral amplifier stage 6. Operational amplifier 5, capacitor C2, and resistors R3 and R4 comprise proportional/integral amplifier stage 6. Operational amplifier 55, capacitor C1, and resistors R1 and R2 comprise differential amplifier stage 54. The gain versus frequency characteristics of proportional/integral amplifier stage 6 and differential amplifier stage 54 are tuned by the combinations of resistors and capacitors chosen according to known methods. The circuit as shown in FIG. 3 responds unacceptably slowly to changes in pressure in the range of about 0–50 mm Hg. To correct for this slow response, automatic gain control circuit (the "AGC") is incorporated in the circuit of FIG. 3 by substituting light dependent resistors ("LDR") for R2 and P3. When system 1 is operating in the range of 0–50 mm Hg pressure, the AGC further boosts the gain of proportional/integral amplifier stage 6 by reducing the resistance value of R3 and simultaneously reduces the gain of differential amplifier stage 54 by reducing the resistance value of R2. This allows proportional/integral amplifier stage 6 to quickly open proportional valve 18 despite its especially slow response to changes in drive signal 12 when system 1 is operating in the range of 0–50 mm Hg vacuum.

Figure 4:
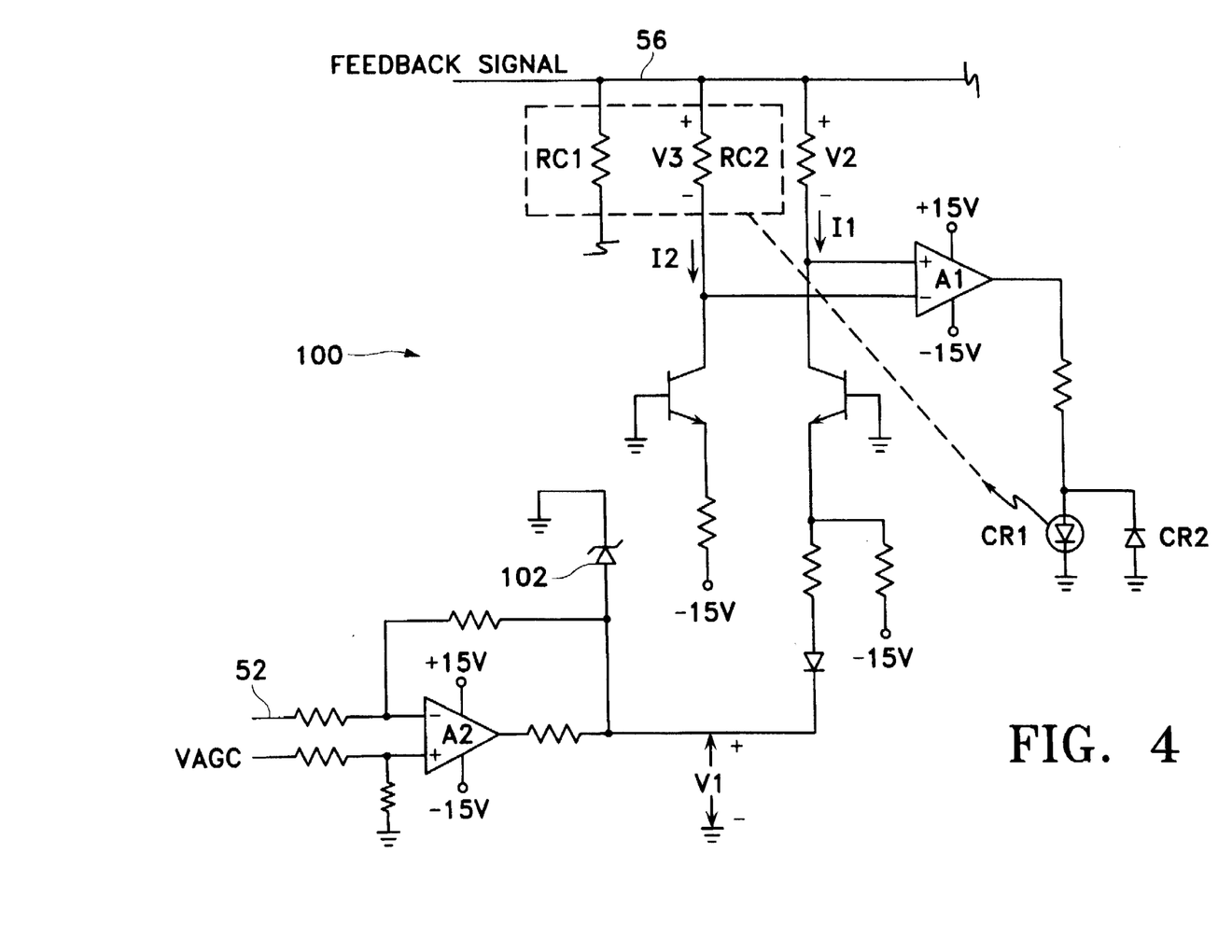
FIG. 4 is a schematic representation of the automatic gain control circuitry of the embodiment of the present invention illustrated in FIG. 2.

As seen in FIG. 4, circuit 100 uses vacuum signal 52 as an input to vary the resistance value of RC1. RC1, RC2, and light emitting diode CR1 are incorporated into a single commercially available LDR package. One suitable LDR package is Model No. VTL5C3/2, available from EG&G Vactec Optoeletronics. LDR RC1 represents the resistor in FIG. 3 to be varied (R2 or R3). The line labeled "FEEDBACK SIGNAL," which is attached to one terminal of RC1, represents feedback signal 56 of FIGS. 2 and 3, and the opposite terminal of RC1 (shown as an unconnected broken line in FIG. 4) is connected to the appropriate node in FIG. 3 (either proportional/integral stage input signal 57 for RC1 when it represents R3 or differential feedback signal 59 for RC1 when it represents R2). As the current supplied to CR1 increases, so does the intensity of light emitted by CR1, which then causes the resistance of RC1 to decrease. A feedback control circuit that is substantially similar to circuit 100 is used to control both R2 and R3, each circuit being tuned to set its respective RC1 to the appropriate value. The AGC is comprised of the combination of beth circuits (each of which is depicted by circuit 100) that control the resistance value of R2 and R3.

The photo-sensitivity characteristics of RC1 and RC2 are matched to each other to within 5%, but the photo-sensitivity of each matched pair may vary from one VTL5C3/2 package to another by as much as 40%. Because RC1 and RC2 are closely matched, circuit 100 incorporates RC2 into a control loop to adjust the current supplied to CR1 to compensate for any unit-to-unit variation. Operational amplifier A2 generates V1 by applying gain to the difference between vacuum signal 52 (from FIGS. 2 and 3) and VAGC, which is calibrated to be equal to vacuum signal 52 when system 1 is generating 0 mm Hg vacuum. Zener diode 102 determines the maximum value of V1. Current I2 through RC2 is set to a predetermined constant value. Current I1 varies proportionally with V1. As V1 and I1 increase, V2 increases and operational amplifier A1 causes the current through CR1 and thus the light output of CR1 to decrease. The reduced light output of CR1 causes the resistance value of RC2 and thus V3 to increase until V3 equals V2. Similarly, decreasing V1 causes the resistance value of RC2 and thus V3 to decrease.

Figure 5:
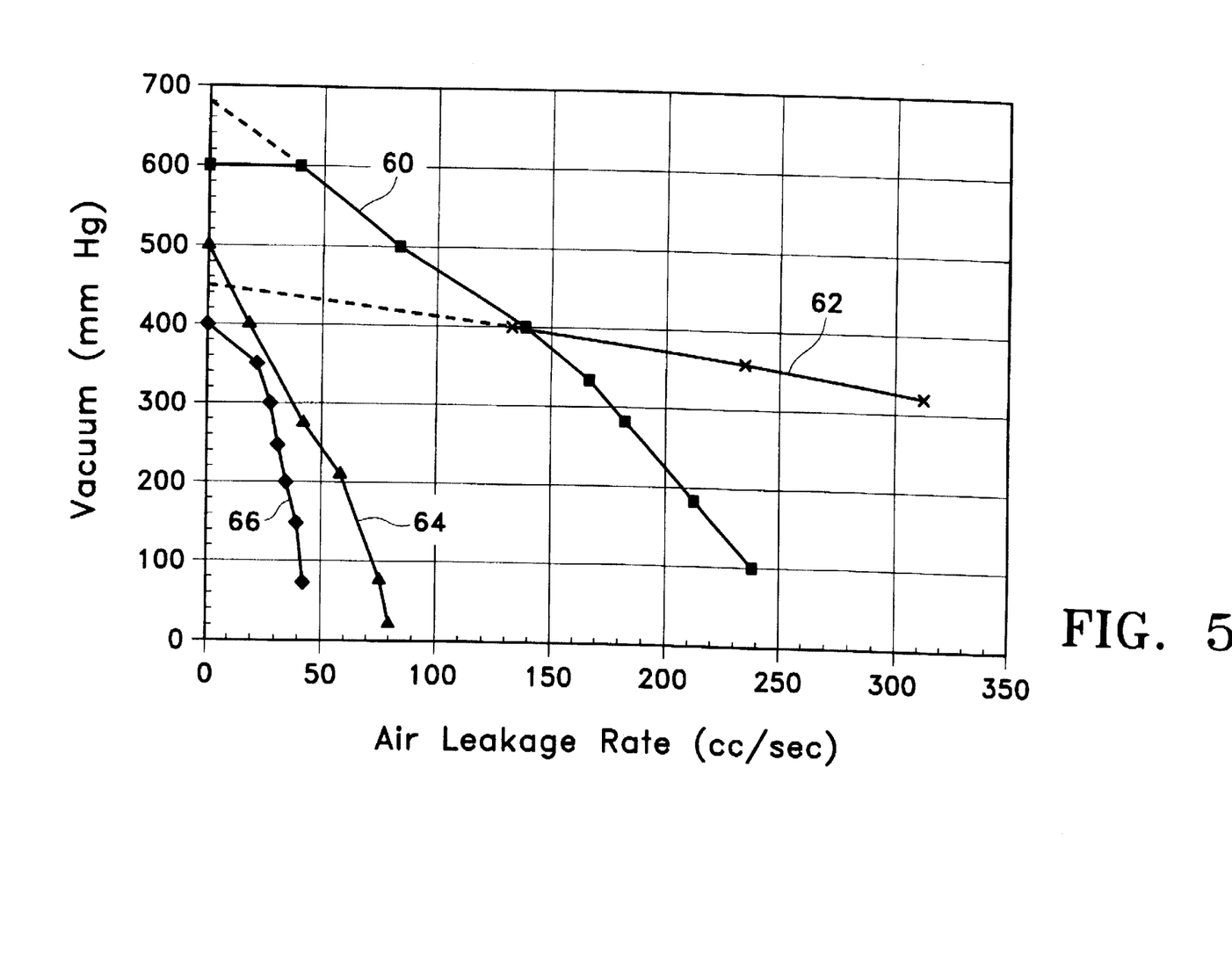
FIG. 5 is a plot of the vacuum generated versus leakage rate for various conventional systems and the embodiment of the present invention illustrated in FIG. 2.

FIG. 5 is a plot of vacuum generated (at about sea level) versus air leakage rate for the present invention and various conventional systems. Trace 60 corresponds to the performance of system 1 (of FIG. 2) and traces 62, 64, and 66 indicate the performance of the prior art Storz, Alcon STTO, and Rogers system respectively. Two important pneumatic performance characteristics are apparent from FIG. 5. First, the resistance of a system to air, leakage is indicated by the slope of each trace. The more gentle the slope, the greater the resistance of the system to air leakage. The resistance of the Storz system is best, the resistance of the Rogers and Alcon STTO systems are worst and the resistance of system 1 is between the extremes.

Second, the maximum vacuum that each system can generate is indicated by the point at which the corresponding trace intersects the y-axis. FIG. 5 indicates that system 1 is most capable of generating vacuum up to about 600 mm Hg. The Rogers, Alcon STTO, and Storz systems are able to generate about 400, 500, and 450 (projected) mm Hg. Became system 1 can generate maximum vacuum of 600 mm Hg, it is able to provide more vacuum than the Storz system for air leakage rates up to about 130 cc/sec, even though it is not as resistant to air leakage as the Storz system. The Storz system, however, consumes about 175 SLPM of air, but system 1 consumes only about 40 SLPM. The pneumatic performance of system 1 is possible became its analog control circuitry can adequately compensate for the nonlinearity and hysteresis of the valve/venturi combination of system 1.

The foregoing is provided for the purposes of description rather than limitation. Changes, modifications, or adaptations may be made to the pressure control system and components described in the foregoing and the remainder of this document without departing from the scope or spirit of the invention.

We claim:

1. A system for controlling a process that responds to changes in a drive signal, comprising:
   a. a means for generating a desired process status signal;
   b. a proportional amplifier stage that generates the drive signal, the proportional amplifier staging including
      i) an inverting input,
      ii) a non-inverting input to which the desired process status signal is connected and
      iii) a first variable resistor;
   c. a process sensor that generates an actual process status signal; and
   d. a differential amplifier stage using the actual process status signal to generate a feedback signal, the feedback signal being connected to the inverting input of the proportional amplifier stage.

2. The process control system of claim 1 in which the differential amplifier stage further comprises a second variable resistor.

3. The process control system of claim 2 in which the first and second variable resistors are light dependent resistors.

4. The process control system of claim 3 further comprising an integral amplifier stage that is connected in parallel to the proportional amplifier stage.

5. The process control system of claim 3 further comprising a means for varying the resistance of the first variable resistor and a means for varying the resistance of the second variable resistor.

6. The process control system of claim 1 further comprising an integral amplifier stage that is connected in parallel with the proportional amplifier stage.

7. A pressure control system comprising:
   a. a means for generating a desired pressure signal;
   b. a proportional amplifier stage that generates a drive signal and includes:
      i) an inverting input,
      ii) a non-inverting input to which the desired pressure signal is connected and
      iii) a first variable resistor;
   c. a pneumatic system comprising:
      i) a regulated high pressure source,
      ii) a proportional valve, the position of which is determined by the drive signal, and
      iii) an output manifold with the regulated high pressure source, the proportional valve, and the output manifold respectively pneumatically connected in series;
   d. a pressure transducer that generates an actual pressure signal in proportion to the pressure in the output manifold; and
   e. a differential amplifier stage using the actual pressure signal to generate a feedback signal, which feedback signal is connected to the inverting input of the proportional amplifier stage.

8. The pressure control system of claim 7 further comprising an ophthalmic surgical instrument connected to the output manifold.

9. The pressure control system of claim 7 further comprising a venturi having a vacuum manifold, which venturi is connected between the proportional valve and the output manifold such that the vacuum manifold is connected to the output manifold.

10. The pressure control system of claim 9 further comprising an ophthalmic surgical instrument connected to the output manifold.

11. The pressure control system of claim 7 in which the differential amplifier stage further comprises a second variable resistor.

12. The pressure control system of claim 11 in which the first and second variable resistors are light dependent resistors.

13. The pressure control system of claim 12 further comprising a means for varying the resistance of the first variable resistor and a means for varying the resistance of the second variable resistor.

14. The pressure control system of claim 7 further comprising an integral amplifier stage that is connected in parallel to the proportional amplifier stage.

* * * * *

UNITED STATES PATENT AND TRADEMARK OFFICE
CERTIFICATE OF CORRECTION

PATENT NO. : 5,674,194
DATED : October 7, 1997
INVENTOR(S) : Christopher C. Jung, et al It is certified that error appears in the above-identified patent and that said Letters Patent is hereby corrected as shown below:

In Col. 4, line 1
delete the word "dosing"
and substitute therefore --closing--.

In Col. 4, line 3
delete the word "dosed"
and substitute therefore --closed--.

In Col. 4, line 23
delete the word "dose"
and substitute therefore --close--.

In Col. 4, line 38
delete the word "Became"
and substitute therefore --Because--.

In Col. 5, line 11
delete the word "dosing"
and substitute therefore --closing--.

In Col. 5, line 21
delete the word "Became"
and substitute therefore --because--.

UNITED STATES PATENT AND TRADEMARK OFFICE
CERTIFICATE OF CORRECTION

PATENT NO. : 5,674,194
DATED : October 7, 1997
INVENTOR(S) : Christopher C. Jung, et al It is certified that error appears in the above-identified patent and that said Letters Patent is hereby corrected as shown below:

In Col. 5, line 26
delete the word "became"
and substitute therefore --because--.

In Col. 6, line 34
delete "P3"
and substitute therefore --R3--.

In Col. 6, line 63
delete "beth"
and substitute therefore --both--.

In Col. 7, line 37
delete "Became"
and substitute therefore --Because--.

In Col. 7, line 43
delete "became"
and substitute therefore --because--.

Signed and Sealed this

Fifteenth Day of September, 1998

BRUCE LEHMAN

Attest:

Attesting Officer

Commissioner of Patents and Trademarks